(12) United States Patent
Renger et al.

(10) Patent No.: US 8,951,281 B2
(45) Date of Patent: Feb. 10, 2015

(54) TUBULAR MEDICAL INSTRUMENT

(75) Inventors: Uwe Renger, Hilzingen (DE); Martin Blocher, Tuttlingen (DE); Uwe Bacher, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 705 days.

(21) Appl. No.: 11/840,465

(22) Filed: Aug. 17, 2007

(65) Prior Publication Data
US 2008/0046002 A1    Feb. 21, 2008

(30) Foreign Application Priority Data

Aug. 17, 2006 (DE) .................... 10 2006 038 517

(51) Int. Cl.
*A61B 17/00* (2006.01)
*A61B 17/29* (2006.01)
*A61B 19/00* (2006.01)

(52) U.S. Cl.
CPC ....... *A61B 17/2909* (2013.01); *A61B 17/00234* (2013.01); *A61B 2017/00477* (2013.01); *A61B 2017/2901* (2013.01); *A61B 2017/292* (2013.01); *A61B 2019/4868* (2013.01); *A61B 2217/005* (2013.01); *A61B 2217/007* (2013.01)
USPC .................. 606/205; 81/3.6; 81/354; 433/4; 606/208

(58) Field of Classification Search
USPC .................. 606/51, 52, 205, 210, 208; 433/4; 81/3.6, 354
See application file for complete search history.

(56) References Cited

U.S. PATENT DOCUMENTS

| 5,439,474 | A | 8/1995 | Li |
| 8,206,410 | B2 * | 6/2012 | Hirai ............................ 606/169 |
| 2005/0021010 | A1 * | 1/2005 | Rothweiler et al. ............. 606/1 |
| 2005/0125027 | A1 * | 6/2005 | Knodel et al. ................ 606/205 |
| 2006/0259070 | A1 * | 11/2006 | Livneh .......................... 606/205 |

FOREIGN PATENT DOCUMENTS

| DE | 14 37 536 | 4/1938 |
| DE | 43 07 539 | 9/1994 |
| DE | 94 18 094 | 1/1995 |
| DE | 19930426 A1 | 1/2001 |
| DE | 200 20 192 | 3/2001 |
| DE | 19948031 A1 | 5/2001 |

OTHER PUBLICATIONS

German Search Report, Feb. 9, 2007, 4 pages.
European Search Report; EP 07 01 5244; Oct. 28, 2008; 9 pages.

* cited by examiner

*Primary Examiner* — Victor Nguyen
*Assistant Examiner* — Kevin Everage
(74) *Attorney, Agent, or Firm* — St. Onge Steward Johnston & Reens LLC

(57) ABSTRACT

The invention relates to a tubular medical instrument having a hollow shaft, a handle equipped with at least two gripping members and positioned on the proximal end of the shaft, and at least one push-pull rod that is mounted in the hollow shaft and has a tool consisting of at least two jaw members. For opening and closing at least one jaw member of the tool, said push-pull rod can be coupled with at last one rotatable gripping member of the handle, and the hollow shaft and handle can be releasably connected to one another by means of a coupling mechanism. To create a coupling mechanism that is simple to operate, it is proposed with the invention that the coupling mechanism should be configured as a combined clamping and snap-on device.

16 Claims, 3 Drawing Sheets

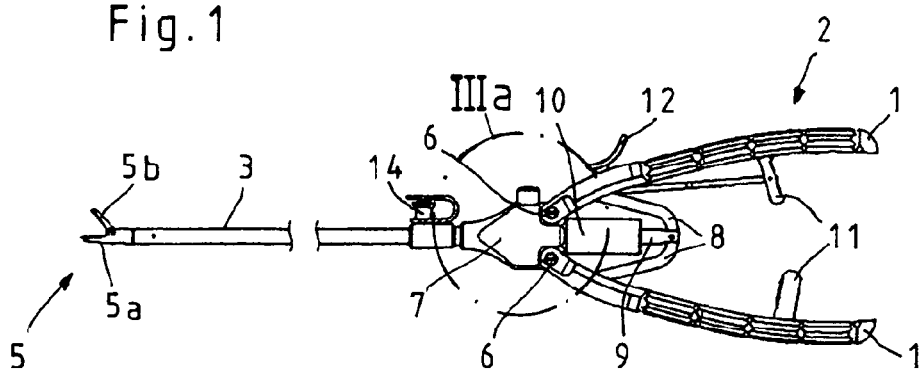
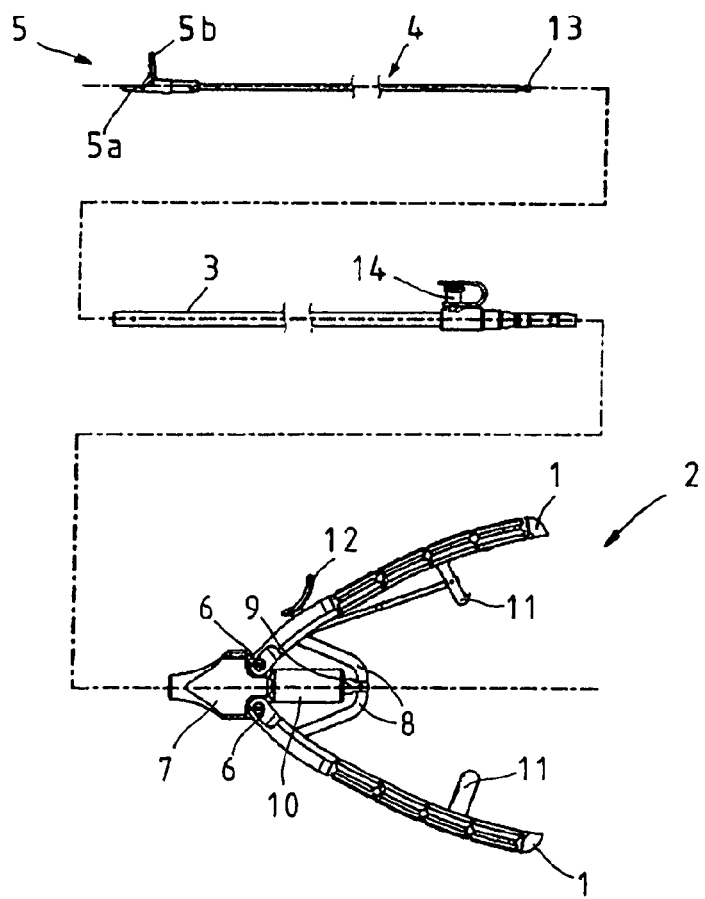

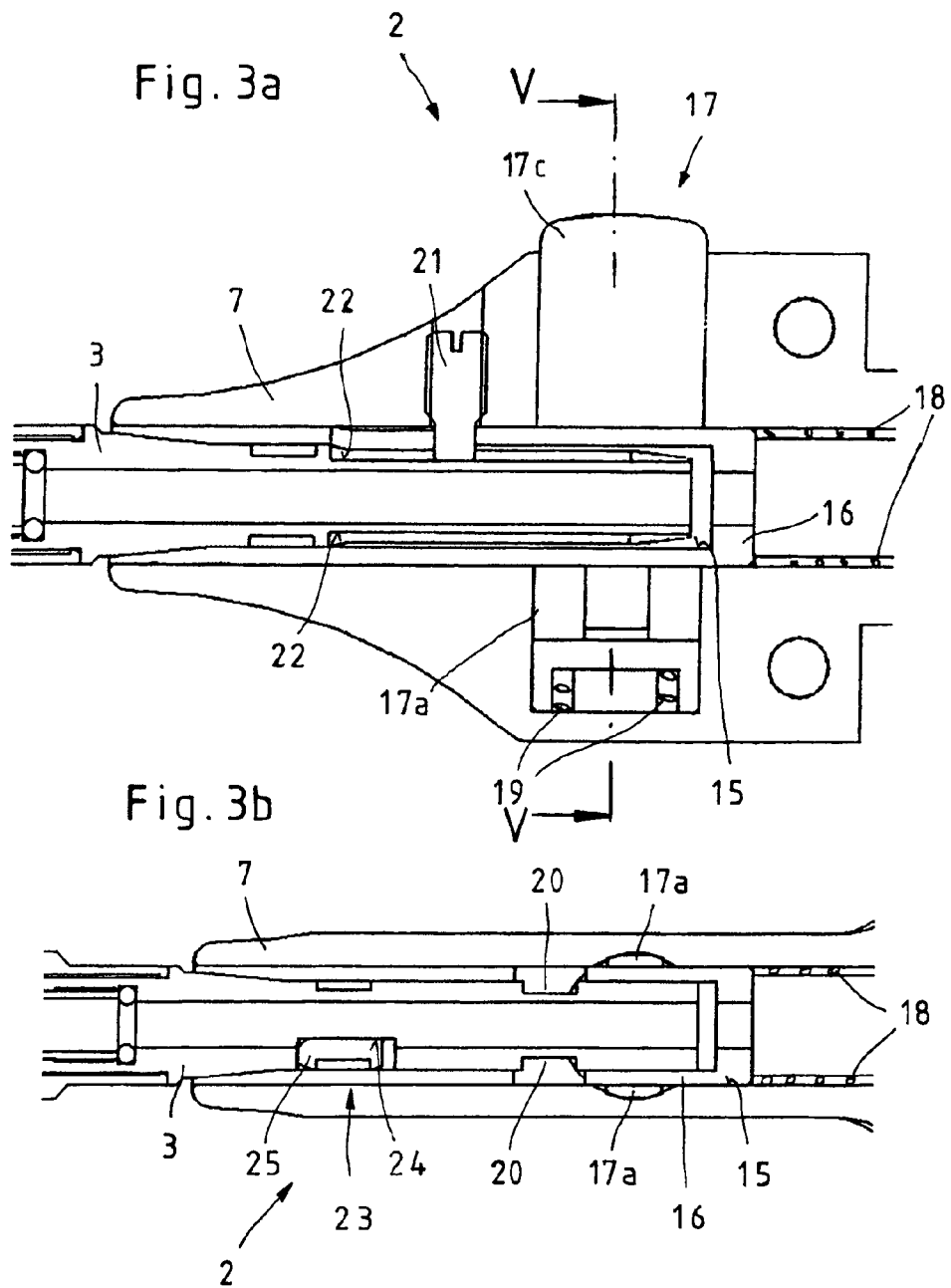

TUBULAR MEDICAL INSTRUMENT

CROSS-REFERENCE TO RELATED APPLICATIONS

The present application claims priority of German patent application No. 10 2006 038 517.9 filed on Aug. 17, 2006, the content of which is incorporated herein by reference.

FIELD OF THE INVENTION

The invention relates to a tubular medical instrument having a hollow shaft, a handle equipped with at least two gripping members and positioned on the proximal end of the shaft, and at least one push-pull rod that is mounted in the hollow shaft and has a tool consisting of at least two jaw members. For opening and closing at least one jaw member of the tool, said push-pull rod can be coupled with at last one rotatable gripping member of the handle, and the hollow shaft and handle can be releasably connected to one another by means of a coupling mechanism.

BACKGROUND OF THE INVENTION

Tubular medical instruments of this type are in use in endoscopic surgery, for instance in the configuration as needle holder. Because of more stringent hygienic standards, it is increasingly frequent that demands are made whereby tubular instruments that include hollow areas, for instance hollow shafts, should be configured so that they can be at least partly dismantled for thorough cleansing and sterilization, preferably sterilization by steam.

In DE 43 07 539 A1, a generic tubular medical instrument, configured as a forceps, is reported. This known tubular instrument can be broken down into three principal units for cleansing and sterilization: the push-pull rod, hollow shaft, and handle. The coupling mechanism for connecting the hollow shaft and handle is configured in this construction as a snap-on connection. Snap-on connections in themselves, as a rule, involve a certain free play when they are not manufactured with extremely minute tolerances, which in turn increase manufacturing costs and make handling difficult during assembly.

It is consequently the object of the invention to perfect a tubular medical instrument in such a way that the hollow shaft and handle can be dissolubly connected to one another by means of a coupling mechanism that, to the greatest extent possible, functions without free play.

SUMMARY OF THE INVENTION

This object is fulfilled through the invention in that the coupling mechanism is configured as a combined clamping and snap-on device.

As a result of the inventive combination of the clamping and snap-on connection, the advantages of both connective techniques are combined, that is, simplicity of installation and dismantling of a snap-on connection and free play of a clamping connection.

In configuring the clamping device, it is proposed with the invention that the proximal end of the hollow shaft should be conical in shape and that an insertion bore-hole should be configured in the handle, open on the distal end and running in the axial direction, for insertion of the proximal end of the hollow shaft, so that the insertion bore-hole comprises a tapering counter-cone that corresponds to itself. This configuration of the conical-shaped shaft end and counter-cone in the insertion bore-hole allows an automatic and nearly play-free coupling of the components that are to be connected together, a coupling that is simple and cost-effective to manufacture on the one hand, and can be easily and quickly assembled and dismantled on the other hand.

According to a practical embodiment of the invention, it is proposed that the counter-cone is configured in a sleeve that is positioned in the insertion bore-hole so that it can be slid in the axial direction. The configuration of the counter-cone in a sleeve that is to be inserted in the insertion bore-hole simplifies the manufacturing of the counter-cone and also allows the adjustment to various cone angles of the shaft end.

It is further proposed with the invention that the sleeve should be positioned in the insertion bore-hole so that it can be axially slid counter to the force of a spring element, so that the sleeve is pre-tensed by the spring element into the installation position that releases the coupling between the hollow shaft and handle. Ability of the sleeve to slide axially simplifies the alignment of the shaft end in relation to the snap-on device, so that manufacturing tolerances can also be easily compensated for, because only the counter-cone of the sleeve is to be manufactured with exact tolerances in order to achieve the clamping effect of the reciprocal conical surfaces, but highly precise tolerances concerning longitudinal configuration of the hollow shaft are not required.

To configure the snap-on device, it is proposed with the invention that in the handle a snap-on element, which can be moved essentially perpendicularly to the insertion bore-hole, should be positioned in the handle, According to a preferred embodiment of the invention it is proposed that the snap-on element should consist of a blocking member as well as a release button that is coupled with the blocking member, so that the snap-on element advantageously is pre-tensed by the spring element in the direction toward the snap-on position. The pre-tensing of the snap-on element in the direction toward the blocking position has the advantage that it automatically reaches the desired snap-on connection as soon as the elements that are to be coupled to one another happen to be in the correct position with respect to the snap-on element.

To ensure secure fixing of the hollow shaft by means of the snap-on connection, in the proximal end of the hollow shaft at least one recess is configured for snap-on insertion of the snap-on element. At least one recess for snap-on insertion of the snap-on element is advantageously configured both in the proximal end of the hollow shat and in the sleeve, in order to be able to fix the conical-shaped shaft end and the counter-cone by means of just one snap-on element.

Correctly seated insertion of the shaft end into the insertion bore-hole, in particular with respect to the alignment to the snap-on device, can be facilitated according to the invention in that at least one guide element is positioned in the handle, to serve to align the proximal end of the hollow shaft in the insertion bore-hole, so that the guide element preferably is configured as a rod or, for instance, as a headless screw that can be screwed into the handle.

According to a practical embodiment of the invention, on the proximal end of the hollow shaft at least one guide groove is configured for insertion of the guide element. Two guide grooves for inserting the guide element are preferably configured opposite to one another on the proximal end of the hollow shaft. The use of two guide grooves opposite one another for inserting the guide element has the advantage that even if only one guide element is to be inserted, the two components to be coupled to one another can be coupled in more than a single position of the components to one another, so that the installation is made easier.

Finally, it is proposed with the invention that the guide element should form a stop for the sleeve and thus should prevent the sleeve from being accidentally pulled out of the insertion bore-hole together with the hollow shaft after release of the snap-on connection.

Further characteristics and advantages of the invention can be seen with reference to the appended illustrations, in which an embodiment of an inventive tubular medical instrument is shown in merely schematic form.

BRIEF DESCRIPTION OF THE DRAWINGS

FIG. 1 shows a schematic side view of an inventive tubular medical instrument.

FIG. 2 shows a schematic side view of the instrument from FIG. 1 in disassembled form.

FIG. 3a shows an enlarged detailed schematic sectional view of detail IIIa from FIG. 1 in a side view during installation.

FIG. 3b presents a view according to FIG. 3a but from overhead.

DETAILED DESCRIPTION OF THE INVENTION

Figure 4A:
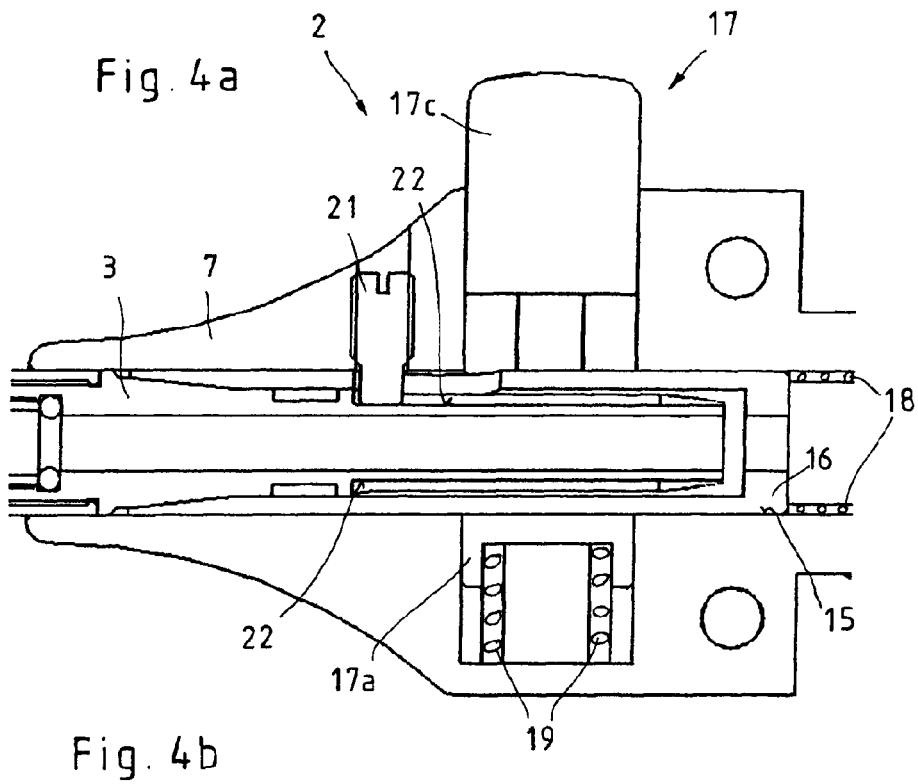
FIG. 4a presents a view according to FIG. 3a, but showing the snapped-together working position.

The tubular medical instrument shown in FIGS. 1 and 2, configured as a needle holder, consists essentially of a handle 2 equipped with two gripping members 1, a hollow shaft 3, and a push-pull rod 4 that can be inserted into the hollow shaft 3 and has on its distal end a tool 5 consisting of two jaw members 5a and 5b.

The tubular medical instrument shown in FIGS. 1 and 2 in the form of a needle holder consists essentially of a handle 2 equipped with two gripping members 1, a hollow shaft 3, and a push-pull rod 4 that can be inserted in the hollow shaft 3 and has on its distal end a tool 5 consisting of two jaw members 5a and 5b.

The three components handle 2, hollow shaft 3, and push-pull rod 4, which are particularly clearly depicted in FIG. 2, can be coupled with one another by coupling and snap-on mechanism in such a way that by actuation of the gripping members 1 of the handle 2 the jaw members 5a and 5b of the tool 5 can be moved between an open and a closed working position, so that the forces exerted by the user upon the gripping members 1 of the handle 2 are transmitted by the push-pull rod 4 to the jaw members 5a, 5b of the tool 5.

In the illustrated embodiment the tool 5 comprises a rigid jaw member 5a and a jaw member 5b that can rotate with respect to the rigid jaw member 5a. It is also possible, of course, to configure both jaw members of the tool 5 as rotatable jaw members 5b.

As can be seen from FIGS. 1 and 2, in the illustrated embodiment both gripping members 1 of the handle 2 are configured as rotatable gripping members 1, which are mounted on a housing 7 of the handle 2 so that they can rotate by means of contact points 6. To convert the rotary motion of the gripping members into a purely axial movement of the push-pull rod 4, as well as for power transmission of the pressure exerted by the user through the handle 2 onto the push-pull rod 4, both gripping members are connected each by an articulated lever 8 with a coupling rod 9, which in turn is coupled directly or indirectly with the push-pull rod 4 by means of a coupling mechanism, so that the coupling of the push-pull rod 4 with the coupling rod 9 and thereby with the handle 1 occurs in the coupling housing 10.

The coupling of the push-pull rod 4 and thus also of the jaw members 5a and 5b of the tool 5 with the gripping members 1 of the handle 2 is designed in such a way that upon pressing together the gripping members 1, the push-pull rod 4 is pulled by the articulated lever 8 and the coupling rod 9 in the axial direction to the proximal end of the instrument. This axial sliding of the push-pull rod 4 to the proximal end of the instrument causes the jaw members 5a, 5b of the tool 5 to move into the closed working position. In this compressed position, the gripping members 1 can be fixed with respect to one another by a stopping device 11, so that the user is not required continuously to exert the pressure on the gripping members 1 of the handle 2. This fixing can be released again by means of an unlocking button 1, which severs the parts of the stopping device 11

Alternatively to the illustrated embodiment, it is also possible, of course, to design the tubular instrument in such a way that the moving of the jaw members 5a, 5b of the tool 5 into the closed working position is effected by sliding the push-pull rod 4 axially to the distal end of the instrument.

The gripping members 1 are advantageously pre-tensed into the open position by a spring element, which for instance can be positioned in the coupling housing 10. As soon as the unlocking button 12 is actuated, this spring element pushes the push-pull rod 4 in the axial direction to the distal end of the instrument, so that the gripping members are pressed apart by means of the coupling rod 9 and the articulated lever 8. This axial sliding of the push-pull rod 4 to the distal end of the instrument causes the jaw members 5a, 5b of the tool 5 to move into the open working position.

Alternatively to the illustrated embodiment of the handle 2 with two rotatable gripping members, it is also possible, of course, to configure just a single gripping member so that it can rotate, whereas the other gripping member is then, for instance, configured as a single piece rigid with the housing 7 of the handle 2. In such a configuration it is possible to couple the push-pull rod 4 directly with the rotatable gripping member 1.

It is further possible to provide overload protection in the coupling area of the push-pull rod 4 with the handle 2, preventing too great an exertion of force onto the push-pull rod 4. Such an overload protection can be configured as an overload spring positioned in the area of the coupling rod 9. To connect the push-pull rod 4 with the handle 2, on the proximal end of the push-pull rod 4 a coupling element 13 is positioned, by which the push-pull rod 4 can be releasably connected with the handle 2.

On the distal side as well, the hollow shaft 3 comprises a coupling or snap-on mechanism in order to be able to couple together the hollow shaft 3 and the push-pull rod 4 that can be inserted into it.

The hollow shaft 3 serving for insertion of the push-pull rod 4 can be coupled with the handle 2 by means of a coupling mechanism, which is positioned in the housing 7 of the handle 2. In the illustrated embodiment of the tubular medical instrument, the hollow shaft 3 also comprises a rinsing connection 14, which serves on the one hand to introduce irrigation fluid during an operation and on the other hand upon which an irrigation house can be connected for cleaning the hollow shaft 3.

The structure of the coupling mechanism for dissoluble connection of the hollow shaft 3 with the handle 2 can be seen in FIGS. 3a through 5.

This coupling mechanism is configured as a combined clamping and snap-on device, whose essential components are the conical-shaped tapering proximal end of the hollow shaft 3, an insertion bore-hole 15 configured in the housing 7 of the handle 2 and running in the axial direction of the tubular instrument, and a sleeve 16 positioned in the insertion bore-hole 15 for configuring the clamping device and a snap-on element 17 that can be mounted perpendicular to the insertion bore-hole 15 for configuring the snap-on device.

To ensure an essentially form-fitted clamping connection between the proximal end of the hollow shaft 3 and the sleeve 16, the inside of the sleeve 16 is configured as a counter-cone tapering in conformity with the cone-shaped end of the hollow shaft 3.

As can further be seen from FIGS. 3a through 4a, the sleeve 16 is positioned so that it can slide axially against the force of a spring element 18 in such a way that the sleeve 16 is pre-tensed by means of the spring element 18 in the distal direction and thus in the direction of the installation position, in which the sleeve 16 is found in the uncoupled position.

Figure 5:
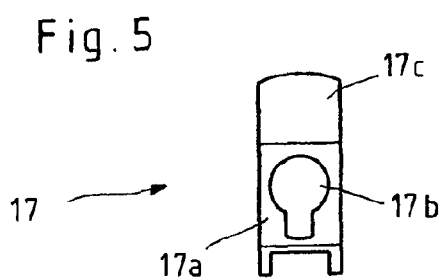
FIG. 5 shows a schematic section along the line V-V according to FIG. 3a, but depicting only the snap-on element.

The snap-on element 17 that forms the snap-on device consists in the illustrated embodiment, as can be seen in particular from FIG. 5, of a locking member 17a, which comprises a through-bore hole 17b that is keyhole-shaped in cross-section for insertion of the sleeve 16 clamped with the proximal end of the hollow shaft 3, as well as a release button 17c that is in active connection with the locking member 17a.

As can further be seen from FIGS. 3a and 4a, the snap-on element 17 is positioned to slide perpendicularly to the insertion bore-hole 15 against the force of a spring element 19 in the housing 7 of the handle 2 in such a way that the locking member 17a is pre-tensed by the spring element 19 in the direction of the snap-on position, in which the locking member 17a grasps the proximal end of the hollow shaft 3 by snap-on locking with it.

The hollow shaft 3 is secured by means of the locking member 17a in the illustrated embodiment through two recesses 20 in each case, which are configured in the proximal end of the hollow shaft 3 as well as congruently in the sleeve 16 and in which the locking member 17a of the snap-on element 17 engages and locks. Reference to FIG. 5 helps to clarify the snap-on connection of the hollow shaft 3 with the locking member 17a of the snap-on element 17 in such a way that the sleeve 16 clamped with the shaft end is mounted in the not yet snap-on connected position in the area of the upper round part of the through-bore hole 17b of the locking member 17a. As soon as the recesses 20 configured in the sleeve 16 and in the shaft end enter into the through-bore hold 17b, the locking member 17a is pressed upward by the spring element 19, so that the sleeve 16 clamped with the shaft end now enters into the narrow lower area of the through-bore hole 17b of the locking member 17a. In this snap-on connected working position shown in FIGS. 4a and 4b, both the sleeve 6 and the hollow shaft 3 are secured in the handle 2 against axial sliding.

To facilitate properly positioned insertion of the shaft end into the insertion bore-hole 15, in particular concerning the alignment of the snap-on device, a guide element 21 is also mounted in the housing 7 of the handle 2 which ensures that the proximal end of the hollow shaft 3 is adjustable in the insertion bore-hole 15. In the illustrated embodiment the guide element 21 is configured as a headless screw that can be screwed into the housing 7 of the handle 2 and engages in a guide groove 22 configured at the proximal end of the hollow shaft 3. Rather than using only one guide groove 22, it is also possible to configure several guide grooves 22 on the proximal end of the hollow shaft 3.

As can be seen from FIGS. 3a and 4a, in the illustrated embodiment two mutually opposite guide grooves 22 are configured on the proximal end of the hollow shaft 3 for inserting the guide element 21. The use of two guide grooves 22 opposite to one another for inserting the guide element 21 has the advantage that, even with only one guide element 21 to be inserted, the two components that are to be coupled together can be coupled to one another not just in a single position of the components, so that the installation is facilitated.

Alternatively to the illustrated embodiment it is also possible, of course, to configure the guide groove for insertion of the guide element 21 as a surrounding groove if the push-pull rod 4 of the medical instrument can rotate around its longitudinal axis.

The joining of the illustrated tubular instrument and, in particular, of the coupling mechanism to connect the hollow shaft 3 with the handle is described below with reference to FIGS. 3a through 5.

In the first step of the installation the push-pull rod 4 and the hollow shaft 3 are coupled with one another, so that, to avoid accidental release of the coupling between the push-pull rod 4 and the hollow shaft 3, the illustrated embodiment comprises a limiting device 23 to restrict the mobility of the push-pull rod 4 inside the hollow shaft 3 in the area of the proximal end of the push-pull rod 4 mounted in the handle 2 and of the hollow shaft 3.

Figure 4B:
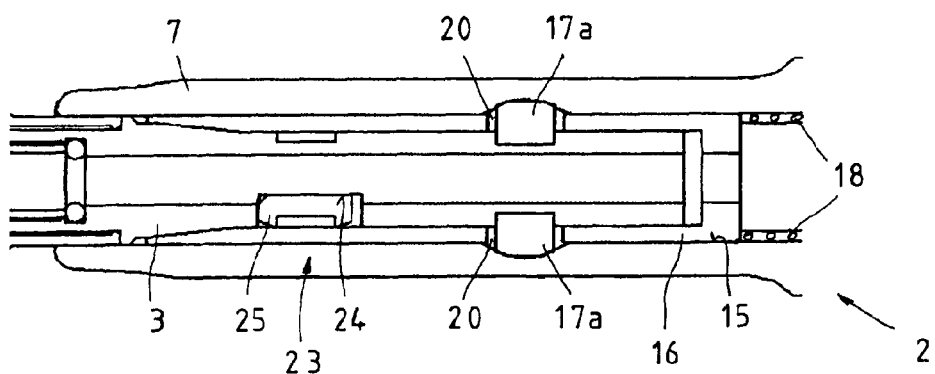
FIG. 4b presents a view according to FIG. 4a but from overhead.

As can be seen from FIGS. 3b and 4b, the illustrated limiting device 23 consists of two contact surfaces configured on the push-pull rod 4 and positioned opposite to one another, which are configured as recesses in the push-pull rod 4, and of a contact element 25 that is mounted in a recess in the hollow shaft 3 and, when the push-pull rod 4 and the hollow shaft 3 are installed, is contiguous, and essentially form-fitted, to a contact surface 24 of the push-pull rod 4.

This limiting device 23, which is effective only with the tubular instrument fully installed, allows an axial motion of the push-pull rod 4 only inside the limited portion of the pathway that is necessary in order to rotate the jaw members 5a, 5b of the tool 5 between the open working position illustrated in FIG. 1 and the closed working position. It becomes impossible to release the coupling between the push-pull rod 4 and the hollow shaft 3 when they are installed, because of the limiting device 23, because the contact element 25 of the limiting device 23, when the hollow shaft 3 is coupled with the handle 2, cannot move radially outward from the recess in the push-pull rod 4. Because of the coupling of the axial displacement of the push-pull rod 4 with the angle of rotation of the gripping members 1 of the handle 2, the limiting device 23, which restricts the axial motion of the push-pull rod 4, thus causes at the same time a limiting of the angle of rotation of the gripping members 1 when fully installed.

In the successive second installation step, the conical-shaped proximal end of the hollow shaft 3 is inserted into the insertion bore-hole 15 configured in the housing 7 of the handle 2, until this end is received in the sleeve 16 positioned in the insertion bore-hole 15, so that the hollow shaft 3 is positioned for purposes of rotating around its longitudinal axis by the guide element 21 in the form of a headless screw is positioned in the insertion bore-hole 15 and in the sleeve 16 for purposes of the snap-on device. Indeed, as soon as the guide element 2 engages in one of the guide grooves 22, the shaft end is positioned correctly and the hollow shaft 3 can no longer be rotated around its longitudinal axis.

Now the conical-shaped shaft end is pressed further into the sleeve 16 until the shaft end locks with the counter-cone of the sleeve 16. Through additional pressure by the hollow shaft 3 in the proximal direction, the sleeve 16 clamped with the shaft end is pressed further inward against the force of the spring element 18 in the proximal direction into the insertion bore-hole 15, until the snap-on element 17 ends the axial sliding of the sleeve 6 by snap-on.

Parallel to this snap-on connection of the proximal end of the hollow shaft 3 with the handle 2, or else subsequent to this snap-on connection, the push-pull rod 4 is coupled with the gripping members 1 of the handle 2 in order to be able to cause an axial sliding of the push-pull rod 4 by means of rotation of the gripping members 1, which sliding in turn causes the displacement of the jaw members 5a and 5b of the tool 5.

As soon as the sleeve 16 clamped with the shaft end has been shoved far enough into the insertion bore-hole 15 so that the recesses 20 configured in the sleeve 6 and in the hollow shaft 3 come to rest at the height of the snap-on element 7, the spring element 9 presses the blocking member 17a of the snap-on element in these recesses and thus blocks any further axial sliding of the sleeve 16 and the hollow shaft 3. Because of the combination of the clamping connection and the snap-on connection, this coupling mechanism ensures the greatest possible free play in the connection.

Disassembly follows then in precisely reverse order of the installation steps by releasing the clamping snap-on connection between the hollow shaft 3 and the handle 2, releasing of the connection of the push-pull rod 4 with the gripping members of the handle 2, to the point of uncoupling the hollow shaft 3 from the push-pull rod 4.

To release the clamping snap-on between the hollow shaft 3 and the handle 2, the snap-on connection is first released by pressing downward on the release button 17c. By actuation of the release button 17c, the blocking member 17a releases the recesses 20 of the sleeve 16 and of the hollow shaft 3 again. As soon as this snap-on connection ceases to exist, the sleeve 16 clamped with the shaft end is pressed by the spring element 18 in the distal direction out of the insertion bore-hole 15.

Pushing the sleeve 6 out of the insertion bore-hold 15 by the spring element 18 simultaneously causes a displacement of the hollow shaft 3 together with the push-pull rod 4 mounted in the hollow shaft 3 in a distal direction. This motion in the distal direction in addition is supported by the coupling rod 9 coupled with the gripping members 1, and said rod is pressed in the distal direction by the gripping members 1 pre-tensed in the open position by a spring element as soon as the clamping snap-on connection between the hollow shaft 3 and the handle 2 is released.

Following the axial sliding of the hollow shaft 3 together with the push-pull rod 4 mounted in the hollow shaft 3, in the distal direction the limiting device 23 is deactivated and releases the coupling between the hollow shaft 3 and the push-pull rod 4 again, because the contact element 25 that is no longer mounted in the handle 2 can now emerge from the recess of the push-pull rod 4 as soon as an axial pushing force is exerted in the distal direction from the proximal end of the push-pull rod 4.

This axial sliding of the sleeve 16 is limited by the guide element 21, which forms a stop for the axial slidability of the sleeve in the distal direction. Now, by pulling in a distal direction, the hollow shaft 3 can be withdrawn from the clamp connection with the sleeve 16.

What is claimed is:

1. A tubular medical instrument comprising:
   a shaft, said shaft being configured as a hollow cylindrical tube;
   a handle having at least two gripping members, said handle mounted on a proximal end of said shaft;
   at least one push-pull rod mounted in said shaft, said at least one push-pull rod having a tool with at least two jaw members, said tool mounted on a distal end of said push-pull rod, wherein said shaft extends over a distal end of said handle up to said tool of said push-pull rod;
   said at least one push-pull rod being disposed inside said shaft about a whole length of said push-pull rod between said handle and said tool, said at least one push-pull rod coupling at least one of said jaw members of said tool with at least one of said gripping members of said handle for opening and closing the at least one of said jaw members;
   a coupling mechanism releasably connecting said handle and said shaft with one another, said coupling mechanism including a combined clamping device and snap-on device; and
   said clamping device comprising the proximal end of said shaft having a cone-shape configuration and an insertion bore-hole disposed in said handle, said insertion bore-hole running in an axial direction and having an opening on a distal end side for inserting the proximal end of said shaft, wherein said insertion bore-hole includes a counter-cone which tapers to provide an essentially form-fitted clamping connection between said cone-shape configuration of the proximal end of said shaft and said counter-cone of said insertion bore-hole of said handle in an assembled form of said instrument.

2. The tubular medical instrument according to claim 1, characterized in that the counter-cone is configured in a sleeve that is positioned in the insertion bore-hole so that the sleeve slides in the axial direction in the insertion bore-hole.

3. The tubular medical instrument according to claim 2, characterized in that the sleeve is mounted in the insertion bore-hole so that the sleeve slides axially against the force of a spring element.

4. The tubular medical instrument according to claim 3, characterized in that the sleeve is pre-tensed by the spring element into an installation position that releases the coupling mechanism between the hollow shaft and the handle.

5. The tubular medical instrument according to claim 1, characterized in that a snap-on element is positioned in the handle so that the snap-on element is displaceable essentially perpendicularly to the insertion bore-hole to configure the snap-on device in the handle.

6. The tubular medical instrument according to claim 5, characterized in that the snap-on element comprises a locking member and a release button coupled with the locking member.

7. The tubular medical instrument according to claim 6, characterized in that the snap-on element is pre-tensed by a spring element in a direction towards a snap-on position.

8. The tubular medical instrument according to claim 5, characterized in that the snap-on element is pre-tensed by a spring element in a direction towards a snap-on position.

9. The tubular medical instrument according to claim 5, characterized in that at least one recess is configured in the proximal end of the shaft for snap-on insertion of the snap-on element.

10. The tubular medical instrument according to claim 9, characterized in that the at least one recess is configured for snap-on insertion of the snap-on element both in the proximal end of the shaft and in a sleeve that is positioned in the insertion bore-hole.

11. The tubular medical instrument according to claim 1, further comprising at least one guide element disposed in the handle, the at least one guide element being adapted to align the proximal end of the shaft in the insertion bore-hole.

12. The tubular medical instrument according to claim 11, characterized in that the at least one guide element is configured as a headless screw.

13. The tubular medical instrument according to claim 12, further comprising at least one guide groove disposed at the proximal end of the shaft, the at least one guide groove being adapted to receive the at least one guide element.

14. The tubular medical instrument according to claim 11, further comprising at least one guide groove disposed at the proximal end of the shaft, the at least one guide groove being adapted to receive the at least one guide element.

15. The tubular medical instrument according to claim 14, characterized in that the at least one guide groove comprises two guide grooves, said two guide grooves are situated opposite to one another at the proximal end of the shaft for insertion of the at least one guide element.

16. The tubular medical instrument according to claim 11, characterized in that the at least one guide element forms a stop for a sleeve that is positioned in the insertion bore-hole.

\* \* \* \* \*